(12) United States Patent
Christensen et al.

(10) Patent No.: US 6,569,128 B1
(45) Date of Patent: May 27, 2003

(54) CATHETER WITH ADJUSTABLE FLOW RESTRICTOR

(75) Inventors: James M. Christensen, Glendora, CA (US); John A. Krug, Orange, CA (US)

(73) Assignee: Advanced Infusion Corporation, Tempe, AZ (US)

( * ) Notice: Subject to any disclaimer, the term of this patent is extended or adjusted under 35 U.S.C. 154(b) by 0 days.

(21) Appl. No.: 09/400,579

(22) Filed: Sep. 22, 1999

(51) Int. Cl.$^7$ .................................................. A61M 5/00
(52) U.S. Cl. .......................................... 604/246; 604/244
(58) Field of Search ................................. 604/244, 246, 604/264, 534, 533, 535, 523, 103, 194, 198, 524, 525, 537, 6.06, 6.09, 6.12, 43, 93.01, 173, 240, 241

(56) References Cited

U.S. PATENT DOCUMENTS

| | | | | |
|---|---|---|---|---|
| 2,874,981 A | * | 2/1959 | Brady ........................ 285/238 |
| 3,094,124 A | * | 6/1963 | Birtwell | |
| 3,951,147 A | | 4/1976 | Tucker et al. ............... 128/260 |
| 4,007,738 A | | 2/1977 | Yoshino ..................... 604/410 |
| 4,239,042 A | * | 12/1980 | Asai ........................ 604/14.11 |
| 4,311,148 A | * | 1/1982 | Courtney et al. ........... 128/348 |
| 4,386,929 A | | 6/1983 | Peery et al. ................ 604/132 |
| 4,627,844 A | * | 12/1986 | Schmitt ..................... 604/264 |
| 4,741,733 A | | 5/1988 | Winchell et al. .............. 604/51 |
| 4,747,621 A | * | 5/1988 | Gans et al. ..................... 285/7 |
| 4,846,812 A | * | 7/1989 | Walker et al. ............... 604/264 |
| 5,049,138 A | * | 9/1991 | Chevalier et al. ........... 604/265 |
| 5,158,553 A | * | 10/1992 | Berry et al. ................. 604/248 |
| 5,222,486 A | * | 6/1993 | Vaughn ................. 128/200.24 |
| 5,358,493 A | * | 10/1994 | Schweich, Jr. et al. ...... 604/264 |
| 5,599,296 A | * | 2/1997 | Spears .......................... 604/26 |
| 5,626,564 A | * | 5/1997 | Zhan et al. .................. 604/164 |
| 5,681,274 A | * | 10/1997 | Perkins et al. .................. 604/8 |
| 5,830,196 A | * | 11/1998 | Hicks ......................... 604/284 |
| 5,876,384 A | * | 3/1999 | Dragan et al. .............. 604/264 |
| 5,891,112 A | * | 4/1999 | Samson ...................... 604/524 |
| 5,899,890 A | * | 5/1999 | Chiang et al. .............. 604/264 |
| 5,902,286 A | * | 5/1999 | Reitz .......................... 604/271 |
| 5,931,865 A | * | 8/1999 | Silverman et al. ............. 623/1 |
| 5,954,694 A | * | 9/1999 | Sunseri ........................ 604/96 |
| 5,997,515 A | * | 12/1999 | de la Torre et al. ......... 604/256 |
| 6,045,547 A | * | 4/2000 | Ren et al. ................... 604/525 |
| 6,053,903 A | * | 4/2000 | Samson ...................... 604/526 |
| 6,152,914 A | * | 11/2000 | Van De Kerkhof et al. 604/533 |
| 6,325,790 B1 | * | 12/2001 | Trotta .......................... 604/523 |

* cited by examiner

Primary Examiner—Brian L. Casler
Assistant Examiner—Kevin C. Sirmons
(74) Attorney, Agent, or Firm—Koppel, Jacobs, Patrick & Heybl; Michael J. Ram

(57) ABSTRACT

An infusion catheter with an adjustable flow contains a flow restrictor tube located in the lumen of the catheter. The flow rate through the infusion catheter can be adjusted by reducing the length of the flow restrictor tube and infusion catheter assembly.

4 Claims, 5 Drawing Sheets

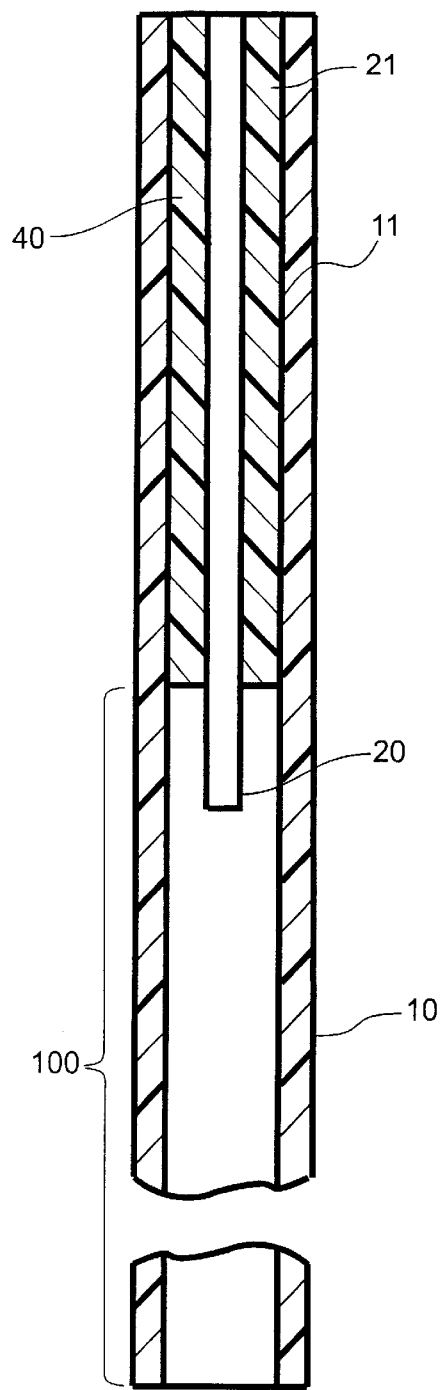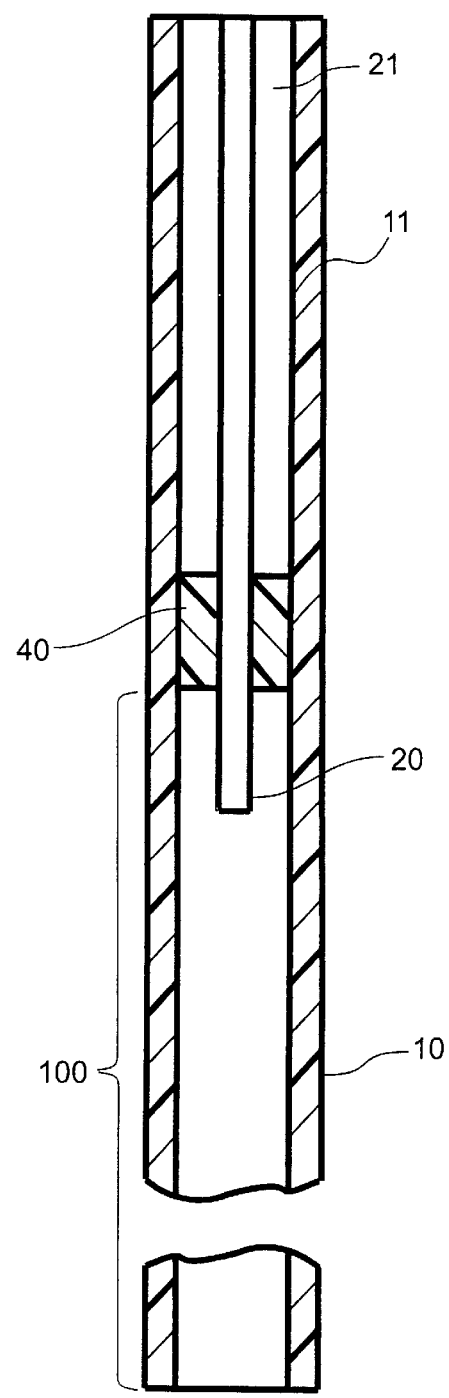
FIG. 2A  FIG. 2B

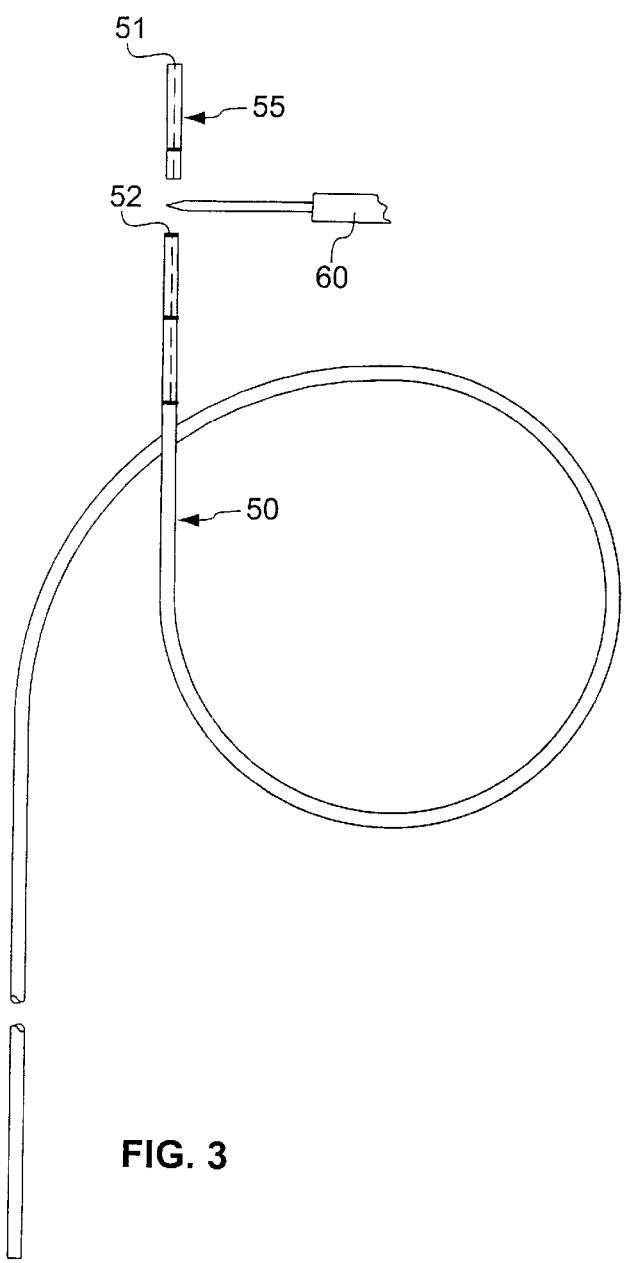
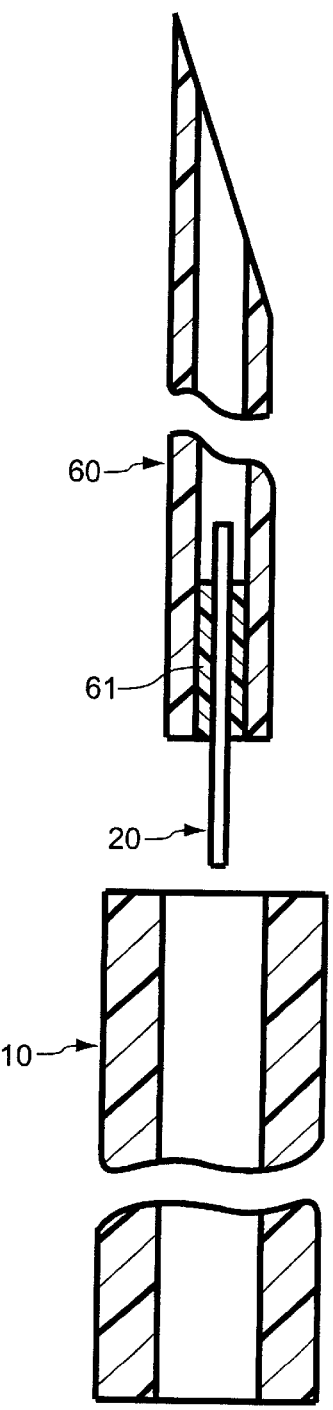
FIG. 3
FIG. 4

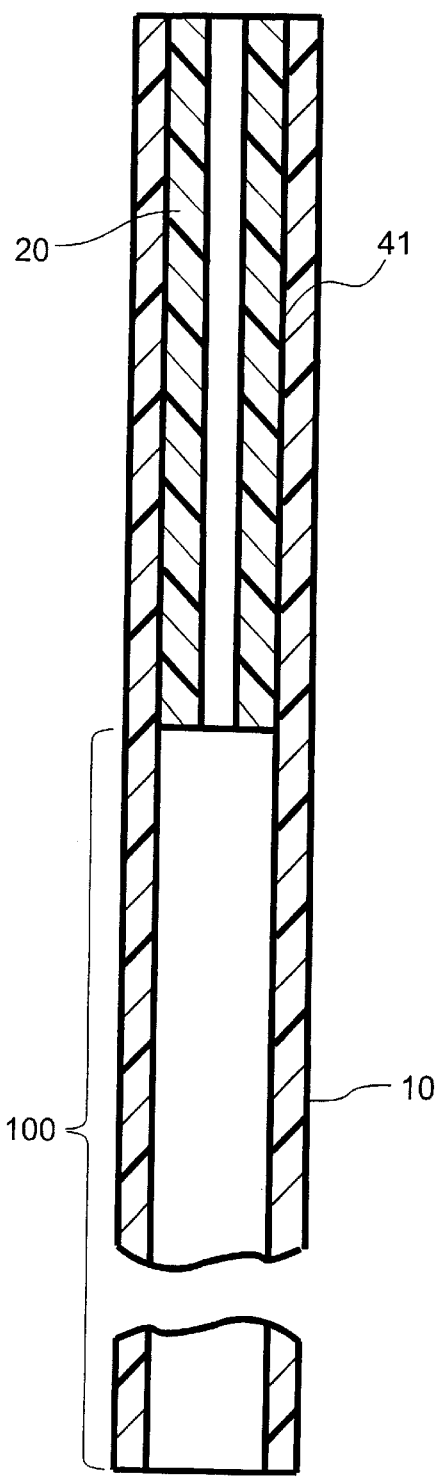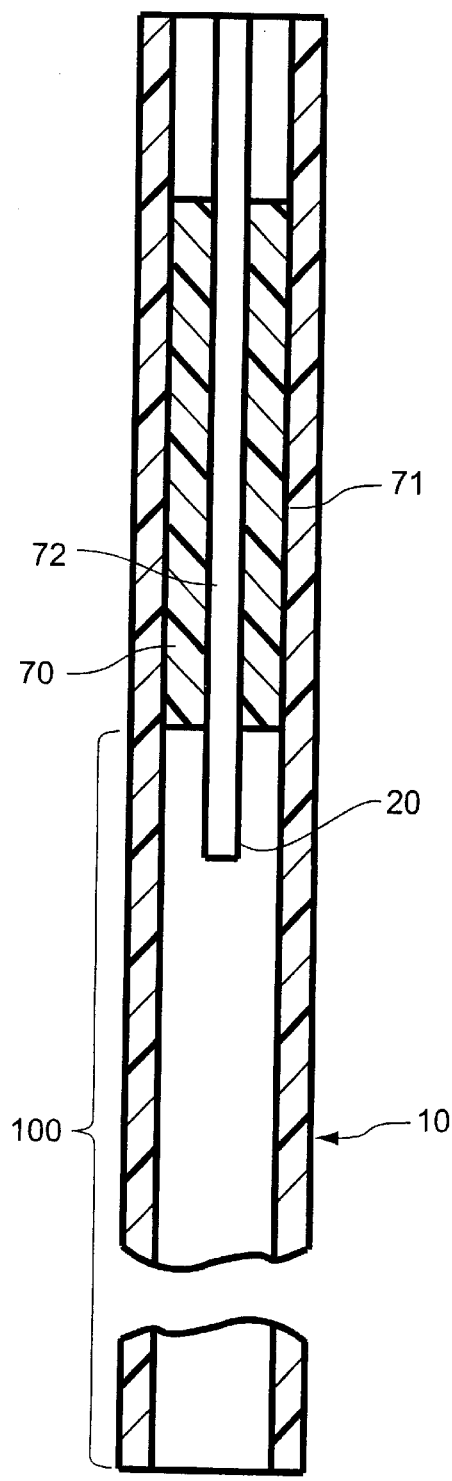
FIG. 5   FIG. 6

CATHETER WITH ADJUSTABLE FLOW RESTRICTOR

BACKGROUND OF THE INVENTION

1. Field of the Invention

The present invention generally relates to a liquid delivery tube, and more particularly, to a catheter for dosing medication which encloses a flow restrictor tube within the catheter lumen.

2. Description of the Prior Art

It is well known that the flow rate of a fluid through a tube can be controlled by a flow restricting orifice, an internal second tube, tube, or micro-passage of various configurations in combination with the first tube. There are several common embodiments of this art in commercial use today. U.S. Pat. No. 3,951,147 to Tucher, et al, describes several flow restrictors including a long stainless steel tube which is wound around an infusion pump body, a long spiral groove formed by inserting a threaded wire into a tube, and other similar configurations.

U.S. Pat. No. 4,386,929 to Peery, et al, discusses a short capillary tube contained within a pump housing for regulating the flow rate of medication dispensed. He also mentions other types of flow restrictors such as porous plugs, fiber bundles, and porous films, all of which are contained within the pump housing.

This prior art suffers from the disadvantage that changing the flow rate requires the use of a different pump. This creates an inventory problem for users who wish to select from a variety of flow rates at the time of application of the infusion pump. In addition, these infusion pumps generally do not provide the capability of delivering fluid to more than one catheter at a time since each catheter would require its own flow restrictor to insure a proper flow rate through the catheter.

U.S. Pat. No. 4,741,733 to Winchell, et al, discloses a flow restrictor placed in the delivery tube system outside the pump body. This system is used where multiple catheters are required to adequately infuse medication into the body. The Winchell flow restrictor consists of a short restrictor tube contained within a plastic housing. Usually the flow restrictor is a glass micro-bore tube.

To vary flow rates, the flow restrictor housing must be removed from the infusion delivery system, and a flow restrictor having a different flow rate added to the infusion system. Branching connectors can also be added. In this way multiple catheters having different flow rates can be achieved. However, it is still necessary that an inventory of flow restrictors having different flow rates be maintained if the user wishes to vary the flow rates at the time of application of the infusion device.

In order to overcome the need to maintain an inventory of catheters or flow restrictors having different flow rates, it is desirable to have a catheter with a flow rate easily adjustable at the time of use. Such a catheter would enable only one catheter to be inventoried yet allow the user to adjust its flow rate to any flow rate desired at the time of use.

SUMMARY OF THE INVENTION

Accordingly, the current invention provides a new and improved catheter for dispensing fluids and medications from an infusion device. A new and improved catheter is provided which contains a flow restrictor within the catheter tube, the flow rate through the catheter being easily adjustable.

In accordance with these and many other objects of the current invention, a catheter tube with a flow restrictor tube located within has a flow rate which is adjustable by trimming the length of the flow restrictor and catheter tube assembly. The tubing could be trimmed at the time of manufacture or could be trimmed at a later time of use. Length markings to aid in trimming the tubing assembly, which are correlated with a flow rate through the catheter, can be placed on the outside of the catheter tubing by ink, or other suitable markings such as imbedding the markings in the tubing wall.

The flow restrictor tubing can be any flexible micro-bore tubing that can be easily trimmed without distorting the trimmed end. The flow restrictor tubing is positioned within the lumen of the catheter tubing so that no fluid will flow between the outside of the flow restrictor tubing and the wall of the lumen of the catheter tubing. The catheter can be attached to the infusion device after trimming by means of a Touhy-Borst connector, or by other suitable means.

As the catheter flow restrictor assembly is shortened by trimming, the flow rate will increase in linear proportion to the initial length of the flow restrictor tubing. For example, if the length of the flow restrictor tubing is cut in half, the flow rate will double.

BRIEF DESCRIPTION OF THE DRAWINGS

The preset invention, together with the above and other objects and advantages, can best be understood from the following detailed description of the embodiment of the invention illustrated in the drawings, wherein:

FIGS. 2a and 2b are cross-section views showing the structure of the catheter and flow restrictor assembly enclosed therein;

FIG. 3 is a side view showing the catheter and flow restrictor assembly being trimmed to increase the flow rate.

FIG. 4 is a cross-section view showing a preferred embodiment of the flow restrictor tube attached to a needle for correction of actual flow rate during manufacture.

FIG. 5 is a cross-section view showing the structure of the catheter and flow restrictor assembly wherein the flow restrictor tube outer diameter is the same as the catheter inner diameter.

FIG. 6 is a cross-section view showing an intermediate tube between the catheter and flow restrictor tubes.

DETAILED DESCRIPTION OF THE INVENTION

Figure 1:
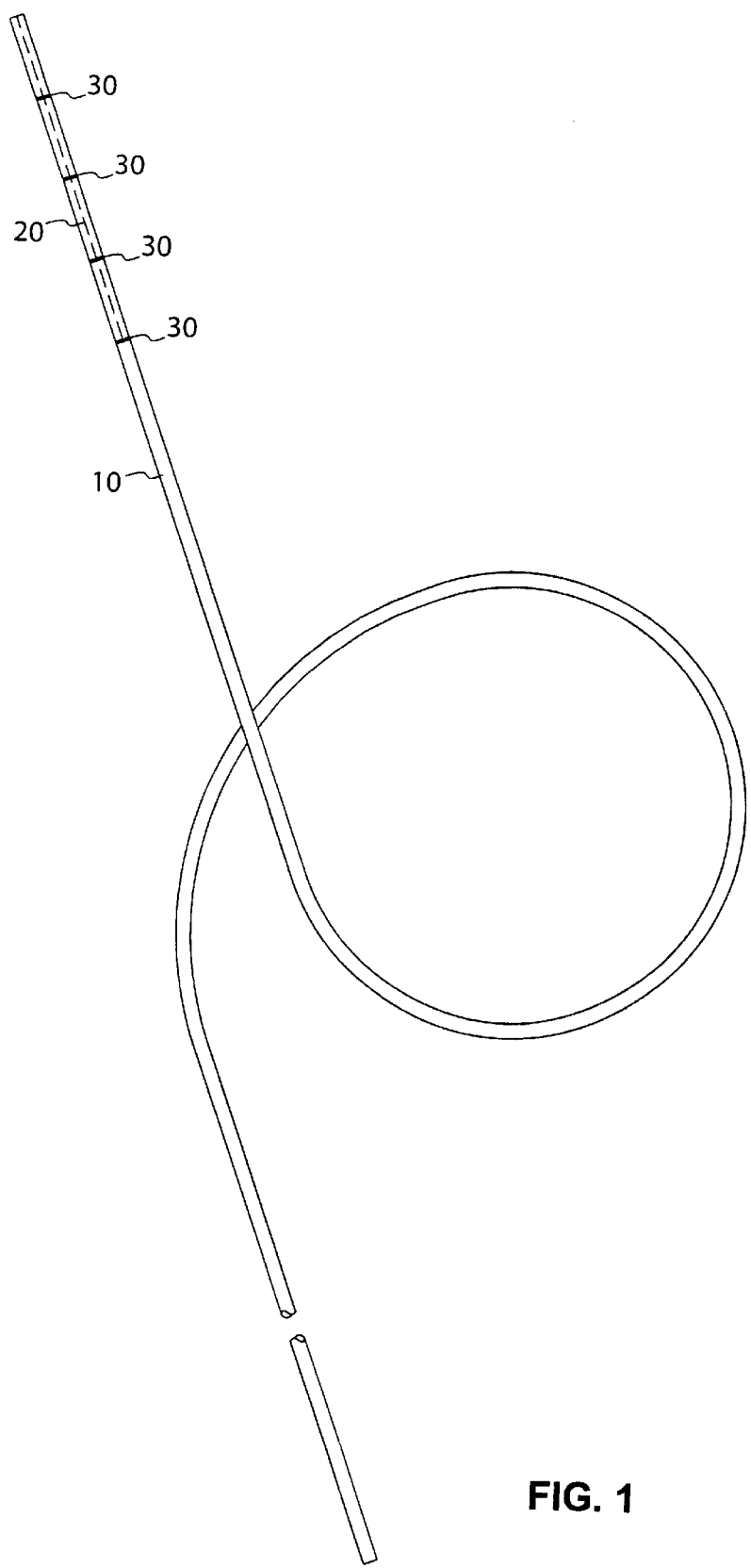
FIG. 1 is a side view of the catheter and flow restrictor assembly embodying the present invention.

Referring now more specifically to FIG. 1 of the drawings, therein is disclosed a catheter generally designated by the reference numeral 10 which contains a flow restrictor tube 20 within it. Along the length of the catheter 10, in the region of the flow restrictor tube 20 containing said flow restrictor 20, can be a series of markings 30 on the catheter or restrictor to aid the user in trimming the catheter to alter flow rate there through.

Catheter 10 can be constructed from a number of materials which are currently used in the industry for catheters.

Typically, these materials include polyvinylchloride, polyurethane, polyethylene, polyamide, silicone elastomer, Teflon®, and other plastics or elastomers. Tubing to be used for catheters is generally extruded, although other methods of manufacture may be used. No requirements are placed on the materials or dimensions of the catheter in the practice of this invention.

Flow restrictor tube 20 can also be constructed from a variety of materials which are currently used in the industry for micro catheters. Typically, these materials include polyimide or polyethylene, although other materials which can be formed into tubing having a small, uniform internal diameter can be used. No requirements are placed on the materials or dimension of the flow restrictor in the practice of this invention other than its ability to be trimmed without its trimmed end becoming deformed.

FIG. 2a shows a cross sectional view of the catheter and flow restrictor tubing assembly. In this view it can be seen that the space between the outside surface 21 of the flow restrictor tube 20 and the inside surface 11 of the catheter 10 is filled with a filler material 40 to block the flow of fluid through this area. This material fills the space along the length of the flow restrictor tube thereby enabling the catheter and flow restrictor tube assembly to be trimmed to the desired length without leaking. Alternatively, FIG. 2b shows the filler material 40 at one end of the flow restrictor tube which will also allow the catheter and flow restrictor tube assembly to be trimmed to the desired length without leaking.

The filler material 40 used to fill the space between the outer surface 21 of the flow restrictor tube 20 and the inner surface 11 of the lumen of the catheter 10 will depend on the materials of construction of each tube and the size of the space. Typically, a material such as silicone elastomer, hot melt adhesive, cyanoacrylate adhesive, or a flexible epoxy would be used.

As an alternative the wall thickness of the flow restrictor tube could be made large enough so that it completely filled the space 41 between the lumen and the outer surface of the flow restrictor tube as shown in FIG. 5. In this case a thin adhesive could be used to seal the space 41 between the tubes. It is also feasible that an intermediate tube 70 as shown in FIG. 6 having an outer diameter 71 approximating the inner diameter of the catheter and an inner diameter 72 approximating the outer diameter of the flow restrictor tube could be used. In this case a thin adhesive could also be used to seal the spaces between the three tubes.

Figure 7:
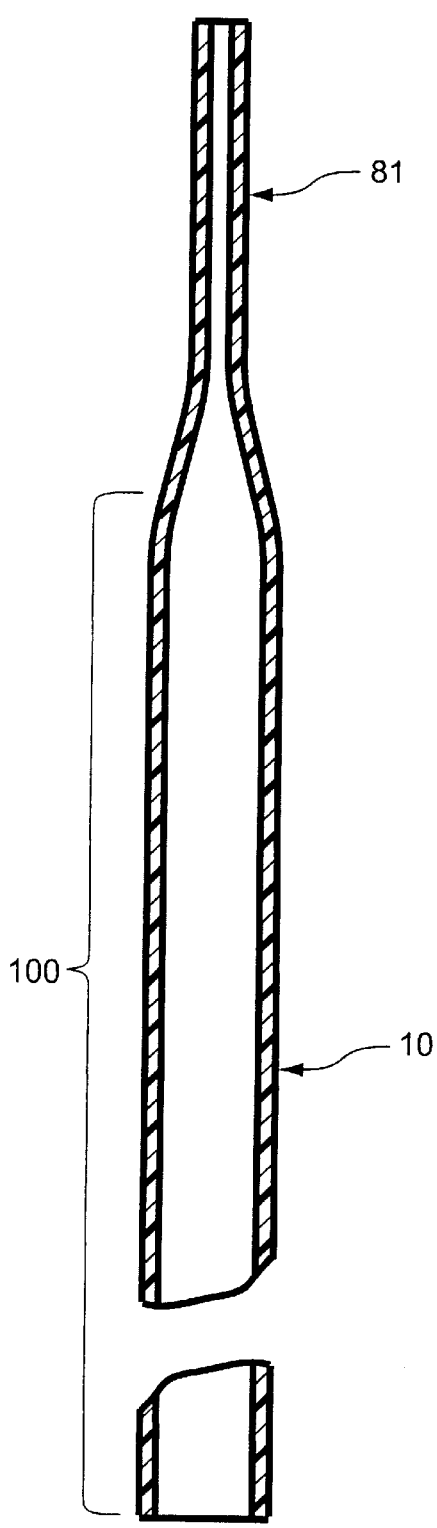
FIG. 7 is a cross-section view showing the catheter tube necked down to form a flow restricting portion in the tube.

In an extension of this invention, it is possible to neck down tubing during the extrusion process or in a secondary stretching process. This would enable a decreased diameter flow restricting segment 81 to be formed in the catheter tubing as shown in FIG. 7. The length of the decreased diameter segment would be made sufficiently long so that it could be trimmed to obtain the desired flow rate through the catheter 10.

Figure 8:
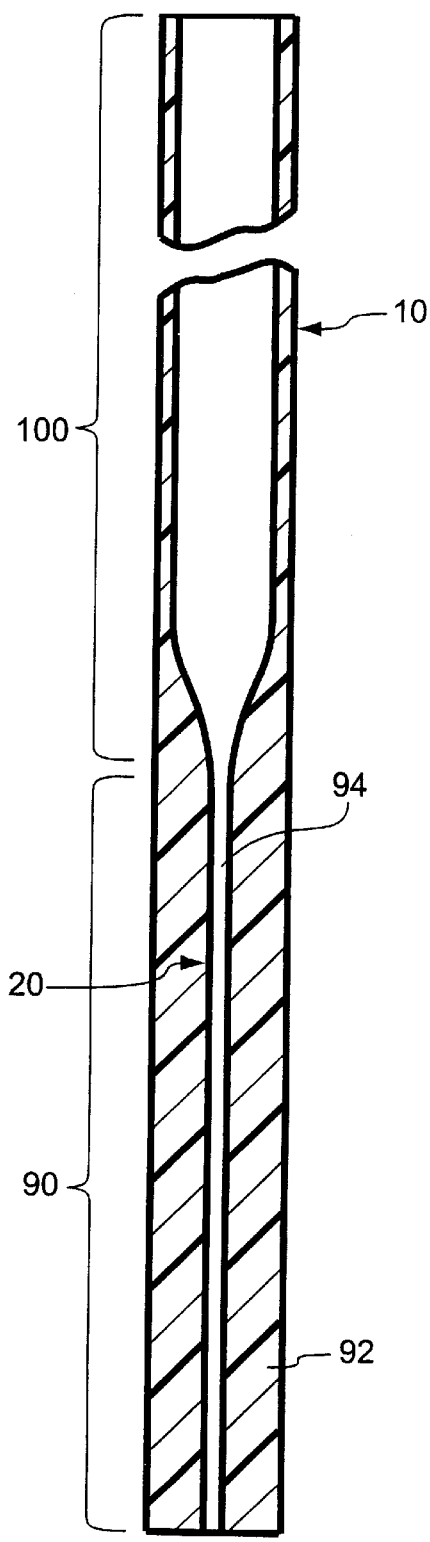
FIG. 8 is a cross-section view showing the catheter tube with a thick wall and a small inner diameter in a second portion.

In a further alternative, as shown in FIG. 8 the tubing can be extruded with a second section 90 with a thick wall 92 and a small lumen 94 sufficient to restrict flow there through. This second section 90 can be cut to a shorter length to increase flow there though.

The dimensions of the flow restrictor tube can be determined from Poiseuille's Law as expressed in the equation:

$$Q = \frac{Pr^4}{8Ln}$$

where Q is the flow rate in cc/sec, P is the pressure drop through the tube in dynes/cm, r is the internal radius of the tube in cm, L is the length of the tube in cm, and n is the viscosity in poise of the fluid flowing through to tube. From this equation it can be seen that flow rate is inversely related to the length of the flow restrictor tube. For example, if the tube length is cut in half, the flow rate doubles. It can also be seen that the flow rate is related to the fourth power of the radius. A small change in the internal diameter of the flow restrictor tube can have a major change on the flow rate. For example, if the internal diameter is increased from 0.0020" diameter to 0.0024" the flow rate will more than double. From this relationship, a suitable flow restrictor tube can be chosen which will provide the desired flow rates and allow accurate trimming to alter the flow rate but not be overly long so that the cost of the device is significantly increased.

FIG. 3 shows the catheter and flow restrictor tube assembly 50 as its length is decreased. A sharp instrument such as the knife blade 60 shown can be used to cut a section 55 from the assembly thereby altering the flow rate through the catheter. Either the trimmed end 52 of the catheter 50 or the uncut end 55 of the catheter 50 can then be attached to an infusion device using any standard attachment means common in the industry such as a Touhy-Borst fitting, or other similar means.

In a preferred embodiment, several catheter and flow restrictor tube assemblies were constructed from 65D durometer polyurethane catheter tubing having an ID of 0.020 inch, an OD of 0.030 inch, and a length of 36 inches. Polyimide tubing of several internal diameters and lengths were assembled into the polyurethane catheter tubing using a cyanoacrylate adhesive. The catheter and flow restrictor tube assemblies were connected to an infusion device operating at a pressure of 6 psi. The flow rate through the catheter and flow restrictor tube assembly is given in the chart below:

TABLE I

Flow Restrictor Tube Length (inch) to Obtain Selected Flow Rate at 6 psi

| ID | 0.5 ml/hr | 1.0 ml/hr | 2.0 ml/hr | 4.0 ml/hr |
| --- | --- | --- | --- | --- |
| 0.0031" | 8.80 | 4.40 | 2.20 | 1.101 |
| 0.0028" | 5.85 | 2.93 | 1.47 | 0.74 |
| 0.0025" | 3.70 | 1.86 | 0.93 | 0.47 |
| 0.0022" | 2.22 | 1.11 | 0.56 | 0.28 |

Typical wall thicknesses of the polyimide inner tube are 0.0003 to 0.0005 resulting in outer diameters from about 0.0028 to about 0.0041. It is possible that minor variances in the internal diameter of the flow restrictor tube will occur due to manufacturing inaccuracies. These variances can cause a large variation in the flow rate through the restrictor tube since flow rate varies as the fourth power of the diameter. During construction of the catheter and flow restrictor tube assemblies, the actual flow rate of the assembly can be measured and the catheter and flow restrictor tube assembly trimmed to obtain a more accurate flow rate. In this way precise flow rate assemblies can be manufactured.

In another preferred embodiment as shown in FIG. 4, the flow restrictor tube 20 is sealed into a needle 60 using a cyanoacrylate adhesive filler material 61. The flow rate of the assembly is then measured by flowing water at 6 psi pressure through the assembly for a period of time. The actual flow rate is then determined, and the length of tubing to be cut from the flow restrictor tube in the assembly is calculated. After the flow restrictor tubing has been trimmed, the polyurethane catheter 10 is placed over the flow restrictor tube and sealed to the needle using cyanoacrylate adhesive.

While the above description sets forth the use of a second tube within a first, outer tube, the invention also contemplates the use of a single catheter tube with a first portion 100 having a typical inner and outer.diameter along most of its length and a second portion 21, 81, 90 with a much smaller diameter along the length thereof, the second portion having an inner diameter and length approximating that of the second tube described above. This can be accomplished while maintaining the outer diameter. Alternatively the catheter tube can be extruded with a desired inner and outer diameter and then a portion stretched to reduce both the inner and outer diameter to produce the desired diameter flow channel, the length of the stretched portion being sufficiently long to allow modification of flow rates, as described above, by cutting off lengths of the smaller diameter portion.

It is evident from the foregoing that there are many additional embodiments of the present invention which, while not expressly described herein, are within the scope of this invention and may suggest themselves to one of ordinary skill in the art. It is therefore intended that the invention be limited solely by the appended claims.

We claim:

1. A fluid delivery tube comprising a first portion with a lumen of a fixed inner diameter extending along the length of said first portion and a second portion having a lumen of a fixed inner diameter smaller than the fixed inner diameter of the first portion, the lumen in the first portion and the lumen in the second portion sharing a common central axis, such that fluid introduced into one of the first portion or the second portion also flows therethrough and then through the other of the second portion or the first portion, the second portion having a length adequate to reduce the flow of fluid passing through the lumen in the first portion, the length of the second portion being reducible according to a predetermined calibration analysis to allow a predetermined increased flow rate of the fluid flowing serially through the first and second portion, wherein the second portion comprises a second, small inner diameter tube positioned within a first tube of an inner diameter substantially equivalent to the outer diameter of the second smaller inner diameter tube and the second portion has an inner diameter of from about 0.0022 inches to about 0.0031 inches and a length which may be reduced by cutting to provide a flow rate through the tube at 6 psi of 0.5 to 4.0 ml/hr.

2. The fluid delivery tube of claim 1, for use in dispensing fluids further including a needle for attaching the fluid delivery tube to an infusion device, the second portion constituting a flow restrictor tube, the flow restrictor tube having a defined length and being sealed to the needle and forming a fluid passage through the needle and flow restrictor tube, the length of said flow restrictor tube capable of being shortened to achieve a desired flow rate through the needle and fluid delivery tube, an outer tube positioned over at least a portion of the flow restrictor tube and sealed onto the needle.

3. A fluid delivery tube comprising a first portion with a lumen of a fixed inner diameter extending along the length of said first portion and a second portion having a lumen of a fixed inner diameter smaller than the fixed inner diameter of the first portion, the lumen in the first portion and the lumen in the second portion sharing a common central axis, such that fluid introduced into one of the first portion or the second portion also flows therethrough and then through the other of the second portion or the first portion, the second portion having a length adequate to reduce the flow of fluid passing through the lumen in the first portion, the length of the second portion being reducible according to a predetermined calibration analysis to allow a predetermined increased flow rate of the fluid flowing serially through the first and second portion, wherein the second portion comprises a second, small inner diameter tube positioned within a first tube of an inner diameter substantially equivalent to the outer diameter of the second smaller inner diameter tube and the second portion has a length of from about 2.22 inches to about 8.8 inches and an inner diameter selected to provide a controlled flow rate of 0.5 ml/hr at a pressure of 6 psi, and wherein reducing the length of said second portion will provide an increased flow rate at 6 psi of up to about 4.0 ml/hr.

4. A fluid delivery tube comprising a first portion with a lumen of a fixed inner diameter extending along the length of said first portion and a second portion having a lumen of a fixed inner diameter smaller than the fixed inner diameter of the first portion, the lumen in the first portion and the lumen in the second portion sharing a common central axis, such that fluid introduced into one of the first portion or the second portion also flows therethrough and then through the other of the second portion or the first portion, the second portion having a length adequate to reduce the flow of fluid passing through the lumen in the first portion, the length of the second portion being reducible according to a predetermined calibration analysis to allow a predetermined increased flow rate of the fluid flowing serially through the first and second portion, wherein the second portion comprises a second, small inner diameter tube positioned within a first tube of an inner diameter substantially equivalent to the outer diameter of the second smaller inner diameter tube and the second portion has a length and internal diameter such that fluid flowing therethrough can be controlled by adjusting the pressure applied to said fluid, such that a fluid delivery rate of from about 0.5 ml/hr to about 4.0 ml/hr can be achieved when a pressure of 6 psi is applied to said fluid.

* * * * *